(12) United States Patent
Frota (10) Patent No.: US 11,110,488 B1
(45) Date of Patent: Sep. 7, 2021

(54) SYSTEMS AND METHODS TO ELIMINATE BUBBLES USING ULTRASONIC ENERGY

(71) Applicant: Rafaela Frota, Boca Raton, FL (US)

(72) Inventor: Rafaela Frota, Boca Raton, FL (US)

( * ) Notice: Subject to any disclaimer, the term of this patent is extended or adjusted under 35 U.S.C. 154(b) by 0 days.

(21) Appl. No.: 17/308,971

(22) Filed: May 5, 2021

(51) Int. Cl.
| | | |
|---|---|---|
| *B06B 1/02* | (2006.01) | |
| *C12M 1/21* | (2006.01) | |
| *G06T 7/00* | (2017.01) | |

(52) U.S. Cl.
CPC .......... *B06B 1/0215* (2013.01); *C12M 41/02* (2013.01); *G06T 7/0008* (2013.01); *G06T 2207/30024* (2013.01)

(58) Field of Classification Search
CPC .... B06B 1/0215; C12M 41/02; G06T 7/0008; G06T 2207/30024
USPC .......................................................... 435/283
See application file for complete search history.

(56) References Cited

U.S. PATENT DOCUMENTS

| | | | |
|---|---|---|---|
| 2012/0046593 A1* | 2/2012 | Oraevsky ........... | A61K 47/6929 604/6.01 |
| 2013/0041311 A1 | 2/2013 | Kohane et al. | |
| 2016/0166716 A1 | 6/2016 | Irudayaraj et al. | |
| 2019/0331512 A1* | 10/2019 | Dixon ................. | G01F 1/663 |

OTHER PUBLICATIONS

Shabashevich et al, Bubble Elimination on the Surface of a Contact Lens Submerged in De-Ionized Water, Rochester Institute of Technology, May 5, 2016.
Chen et al, The dynamic behavior of microbubbles during long ultrasound toneburst excitation: mechanistic insights into ultrasound-microbubble mediated therapeutics using high-speed imaging and cavitation detection, Ultrasound Med Biol., Nov. 18, 2015.

* cited by examiner

*Primary Examiner* — Amandeep Saini (57) ABSTRACT

A system to reduce surface bubbles from cell culture media using ultrasonic pulses is disclosed. The system includes a plurality of ultrasonic transducers, a photodetector, a camera, a control circuit, and a cell culture container that includes a cell culture media. The control circuit is communicatively coupled to the plurality of ultrasonic transducers, the temperature sensor, and the camera. The photodetector is used to determine a presence of a surface bubble on the cell culture media. The camera is used to determine a location of the surface bubble when the presence of the surface bubble is determined. The plurality of ultrasonic transducers is used to position an ultrasonic pulse at the location of the surface bubble and thereby reduce the presence of the surface bubble on the cell culture media when the location of the surface bubble is determined.

18 Claims, 9 Drawing Sheets

SYSTEMS AND METHODS TO ELIMINATE BUBBLES USING ULTRASONIC ENERGY

FIELD OF THE INVENTION

The present disclosure relates generally to ultrasound. More specifically, the present disclosure describes systems and methods to eliminate bubbles using ultrasonic energy.

BACKGROUND OF THE INVENTION

In the nineteenth century, plant tissue cultivation was first developed in an attempt to grow plant tissue in-vitro (outside the body of an organism). Since then, science has made strides in advancements surrounding tissue culture done in-vitro to simulate the environmental factors found in-vivo (inside the body of an organism). This practice has significantly contributed to improvements in academic and social understanding pertaining to the many facets of biology and chemistry alike, however, its methodology poses challenges. A significant challenge lies in the almost inevitable forming of air bubbles in cell culture media solutions. As such, air bubbles disturb homogenous cell adhesion in cultured media, thereby hindering cell attachment, increasing sample contamination risk, limiting microscopic visibility, and affecting the solution's alkalinity. There exists a clear need in the art to address this challenge and safely eliminate air bubbles in cell cultures.

BRIEF DESCRIPTION OF THE DRAWINGS

Some of the embodiments will be described in detail, with reference to the following figures, wherein like designations denote like members, wherein.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of systems and methods to eliminate bubbles using ultrasonic energy, embodiments of the present disclosure are not limited to use only in this context. The instant disclosure seeks to provide systems and methods that use ultrasonic energy to eliminate air bubbles from cell culture media without damaging the respective cells. The instant disclosure seeks to provide an array of in-phase ultrasonic transducers to generate a hyper-focused ultrasonic beam to burst air bubbles that exist on, or near, the surface of solution samples.

In the nineteenth century, plant tissue cultivation was first developed in an attempt to grow plant tissue in-vitro (outside the body of an organism). Since then, science has made strides in advancements surrounding tissue culture done in-vitro to simulate the environmental factors found in-vivo (inside the body of an organism). This practice has significantly contributed to improvements in academic and social understanding pertaining to the many facets of biology and chemistry alike, however, its methodology poses challenges. A significant challenge lies in the almost inevitable forming of air bubbles in cell culture media solutions. As such, air bubbles disturb homogenous cell adhesion in cultured media, thereby hindering cell attachment, increasing sample contamination risk, limiting microscopic visibility, and affecting the solution's alkalinity. There exists a clear need in the art to address this challenge and safely eliminate air bubbles in cell cultures.

Ultrasound has been widely accepted and used in medicine for therapeutic purposes since the 1950s, where low intensity-pulsed ultrasonic pulses ("LIPUS") were first used to treat conditions such as tendinitis or bursitis. In the decades that followed, the use of ultrasonic energy continued to expand, with high pressure-amplitude shock waves being applied to varying medical needs, including mechanically eliminating kidney stones, removing cataracts, and even healing bone fractures. More recently, some researchers have reverted to LIPUS and demonstrated that low intensity-pulsed ultrasound can be used to perform medical procedures focused on selectively destroying cancer cells without harming surrounding, healthy cells. This disclosure seeks to burst air bubbles found in cell culture samples by using a proposed LIPUS frequency range corresponding to the natural resonant frequency of respective air bubbles.

Figure 1:
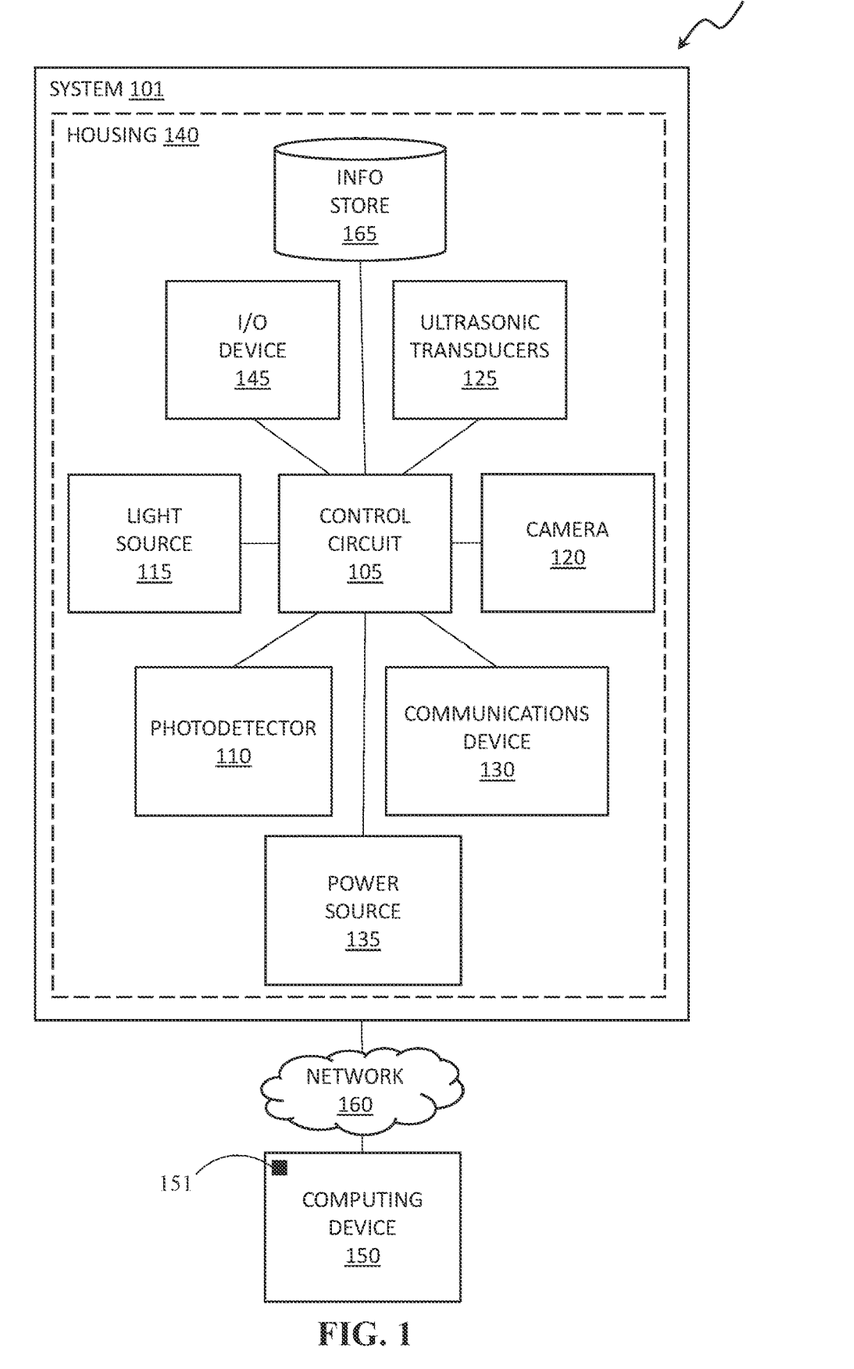
FIG. 1 depicts a block diagram of an environment to reduce surface bubbles from cell culture media using ultrasonic pulses, according to some embodiments.

FIG. 1 depicts a block diagram of an environment, generally 100, to reduce surface bubbles from cell culture media using ultrasonic pulses, according to some embodiments. The environment 100 includes a system 101 and a computing device 150 communicatively coupled via a network 160. Network 160 can be compatible with a variety of frequencies, such as those associated with Bluetooth, Wi-Fi, LTE, cellular, radio, microwave, as well as wireless communication. In general, network 160 can be any combination of connections and protocols that will support communications between the system 101 and the computing device 150. The system 101 preferably includes a plurality of ultrasonic transducers 125, a photodetector 110, a camera 120, a communications device 130, a light source 115, an info store 165, a I/O device 145, and a power source 135 all interconnected to a control circuit 105 and included in housing 140. As used herein, the control circuit 105 can be one or more control circuits known in the art that can be configured to perform one or more steps, processes, functions, and/or methods of the instant disclosure. The power source 135 can be any power source known in the art and includes primary batteries, secondary batteries, and capacitors. For example, the power source 135 is preferably a power delivery subsystem that is configured to ensure that components of the system 101 consistently receives the necessary voltages.

The system 101 is designed to be easily stored, with the housing 140 preferably configured to have a cylinder shape that couples the design of the standard petri dish (e.g., the cell culture container 215) used for cell cultures (e.g., 100 mm×4, 90 mm×4, 60 mm×4) within a rectangular external housing. To be sure, the housing 140 can have any shape that facilitates one or more embodiments of the instant disclosure. The system 101 can be operated via the I/O device 145. The I/O device 145 can include one or more devices that receive and/or receives signals or data from the control circuit 105. In preferred embodiments, the I/O device 145 is a touchscreen interface mounted on or positioned proximate to the exterior of the housing 140. The camera 120 is positioned inside the housing 140 to allow for a live feed of the petri dish (e.g., the cell culture container 215) to be transmitted to the computing device 150 for display via mobile phone application 151, while improving the detection and elimination of air bubbles inside the device. The user interface 151 is a computer program or software application or mobile application designed to run on the computing device 150 and communicate with the system 101, according to certain embodiments. Additionally, the I/O device 145 can include an infrared temperature sensor that is integrated into the system 101 and activated once operation begins. In preferred embodiments, the temperature sensor is put into place to provide characterization metrics for different cell culture types and to record any variation in cell culture temperatures. Although surface bubbles in cell cultures is a much more sensitive environment than the above industrial examples, the same underlying physical forces can be utilized, which is exactly what the system 101 achieves. Most importantly, the ultrasonic transducers 125 do not need to come into contact with the solution. In the following few sections, each of its subsystems and components are detailed.

Figure 2:
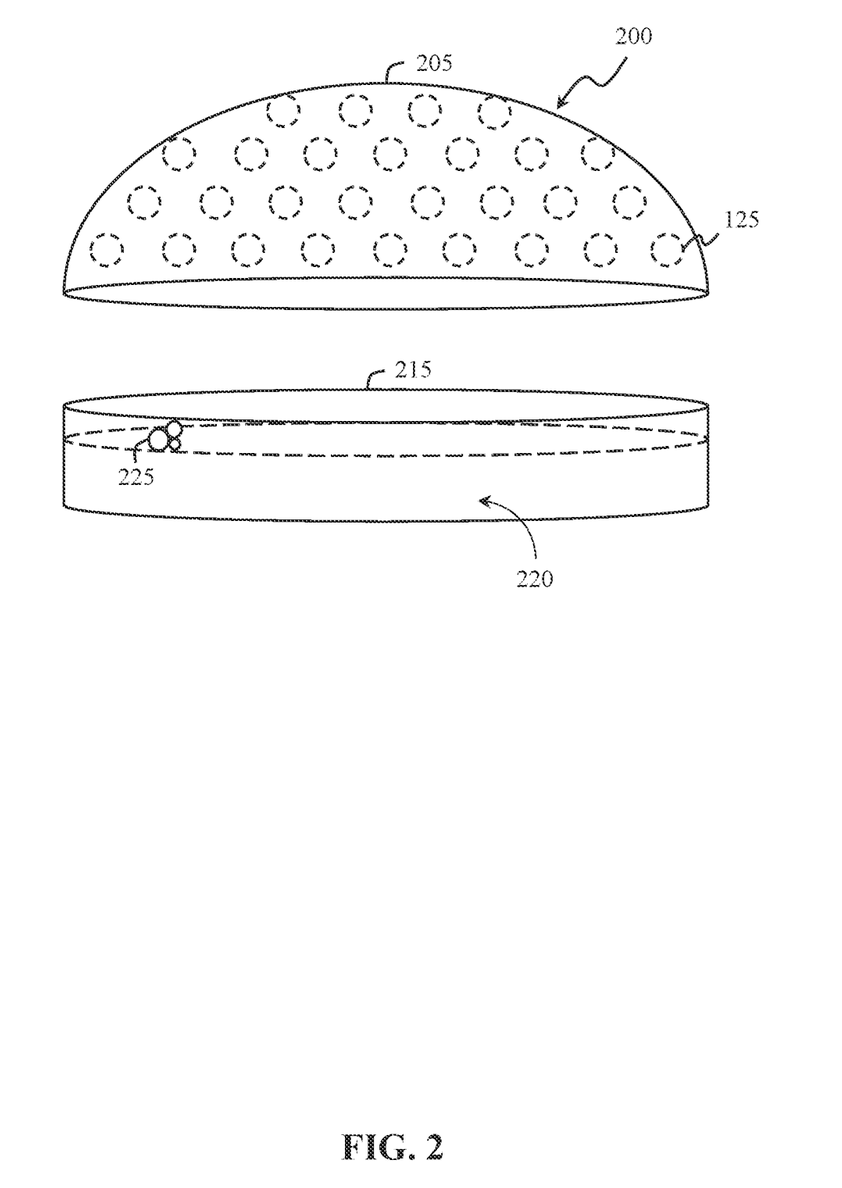
FIG. 2 illustrates a concave array positioned proximate to a cell culture container, according to other embodiments.

FIG. 2 illustrates a concave array 200 positioned proximate to a cell culture container 215, according to other embodiments. The concave array 200 is an in-phase parametric concave ultrasonic transducer array system that creates one, focused standing sound wave. The concave array 200 includes a concave dish 205 and the ultrasonic transducers 125 that are arranged therein and combine to produce a sound wave. The ultrasonic transducers 125 are each typical piezoelectric ultrasonic transducers that can achieve up to 100 MHz. For example, each ultrasonic transducer 125 can have a resonant frequency of 40 kHz and, when arranged in the concave dish 205. The cell culture container 215 includes cell culture media 220, which has bubbles 225 positioned thereon. Nonlinear acoustics is governed by Berktay's expression (defined in Equation 1), $$p_2(x, t) = K \times P_c^2 \times \frac{\partial^2}{\partial t^2} E^2(x, t) \qquad \text{Eq. [1]}$$

where $p_2(x,t)$ is the audible secondary pressure wave, K represents miscellaneous physical parameters, $P_c$ is the sound pressure level of the ultrasonic carrier wave, and $E^2(x,t)$ represents the envelope function. Berktay's expression states that the audible demodulated output signal, or ultrasonic pressure wave is proportional to twice the differentiated, squared input signal, or envelope function. The underlying principle between this nonlinear behavior resides in the interaction between the ultrasonic tones in the air that mix to produce sum and difference frequencies via the principle of superposition. Here, each ultrasonic transducer 125 is in-phase and propagates (e.g., using ultrasonic beam focusing) to a focus point region respective to the position of the cell culture media container 215 inside the housing 140. The focused beam will have a respective frequency that matches the resonant frequency of respective air bubbles found in the cell culture media solution. The resonant frequency of air bubbles is influenced by different environmental characteristics related to specific chemical, pressure, and temperature metrics, but can be calculated via the analytical equation derived by Christopher Brennen (defined in Equation 2), where the natural (or resonance) radial frequency $\omega_n$ of bubbles is seen as a function of environmental characteristics including fluid density $\rho_L$, mean pressure $p_\infty$, vapor pressure $p_v$, surface tension S, equilibrium bubble size $R_e$, and constant k.

$$\omega_n = \left\{ \frac{1}{\rho_L R_e^2} \left\{ 3k(p_\infty - p_V) + 2(3k-1)\frac{S}{R_e} \right\} \right\}^{\frac{1}{2}} \qquad \text{Eq. [2]}$$

Figure 3:
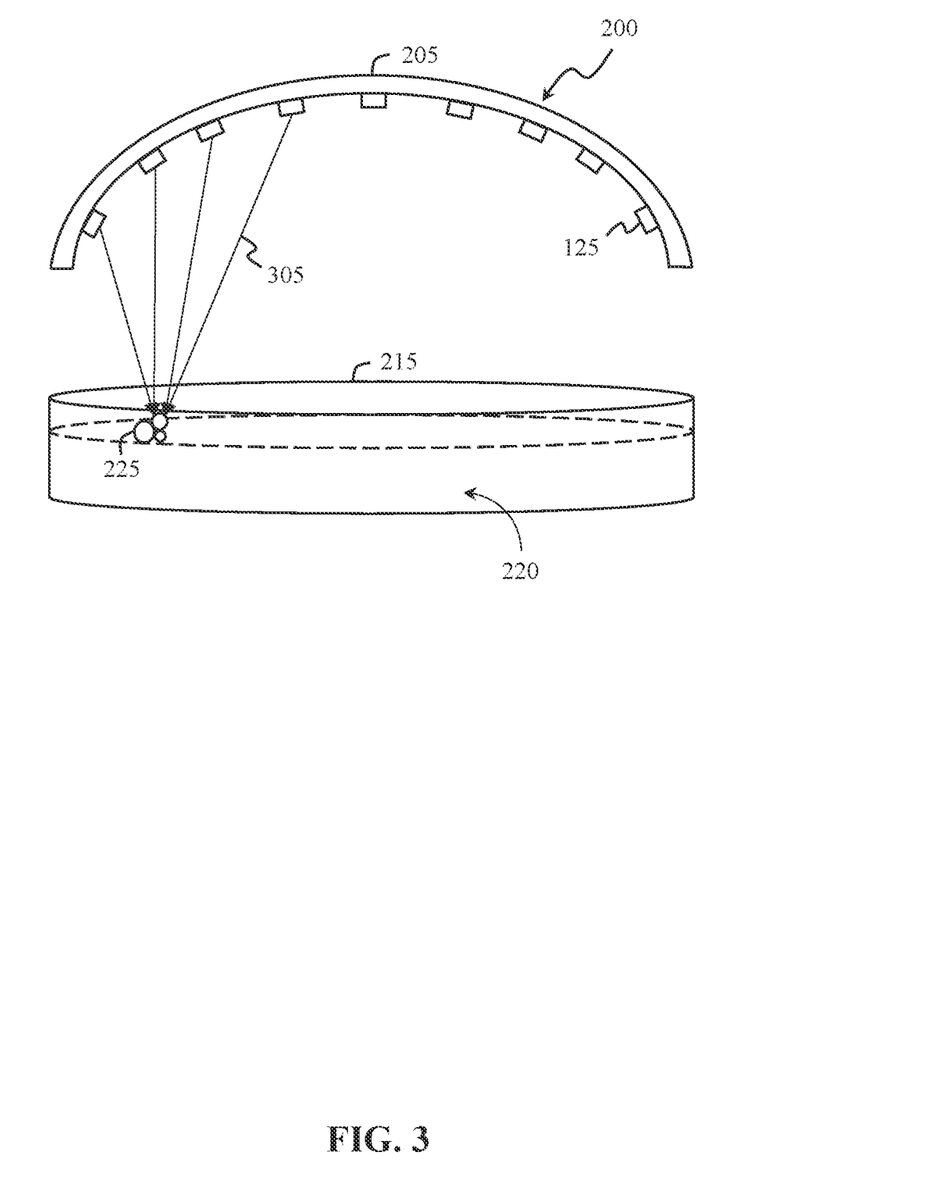
FIG. 3 illustrates a cut-through view of the concave array of FIG. 2, according to certain embodiments.

The challenge in using the ultrasonic beam focusing method lies in being able to successfully phase each ultrasonic transducer 125 so that a narrow, focused standing wave 305 can be outputted from the concave array 200 as shown in FIG. 3. As used herein, the terms "beam", "pulse", and "wave" are used interchangeably. However, through the use of op-amps, timers, and manipulating respective element duty cycles, appropriate phasing can be achieved. Most commonly, amplitude modulation may be used to drive the signal of the ultrasonic carrier wave and influence its direction. The direction of the emitted focused ultrasound beam produced from the concave array 200 is expressed by Equation [3]:

$$\theta_N = \arcsin\frac{cD + N\lambda}{d} \qquad \text{Eq. [3]}$$

$(N = 0, \pm 1, \pm 2, L)$ where D refers to the delay time between the transducers for the directivity control, c refers to the speed of sound, ON refers to the aiming direction, and refers to the incident wavelength.

The ultrasonic transducers 125 require an oscillating input signal to produce ultrasound wave. For example, the ultrasound wave undergoes pulse width modulation to provide a square wave characteristics of respective wave frequency to the power signal obtained from the power supply 135.

The system 101 also utilizes image processing in the furtherance of surface bubble reduction. For example, the system 101 can include one or more of the camera 120 to capture images of the surface bubble 225 of the cell culture container 215. The camera 120 is a typical camera known in the art that captures images using visible light. Image processing occurs once an image is captured. Captured images are preferably converted to a raster image (i.e., an image compiled using pixels, or tiny dots, containing unique color and tonal information that come together to create the image). The raster image is subsequently processed to maximize its contrast. For example, a blue color filter is preferably applied to the raster image to maximize its contrast. Images are captured, processed, and compared between each operation cycle of the device; the percent difference in pixels is calculated for each subsequent capture. This system identifies the presence of bubbles with 98% accuracy. To be sure, applicable filter colors include, but are not limited to, red, and green. However, such filters have proven to be less effective in yielding high contrast within the captured image when the inside of the housing 140 is illuminated with the red, 625 nm LED. It is important to note that the efficacy of this system relies in the comparison of initial base value pixel count readings and final pixel count readings. These measured values are then compared to calculate a percent difference that subsequently triggers the device's operational cycle when the percent difference is greater than a threshold percentage.

Figure 5:
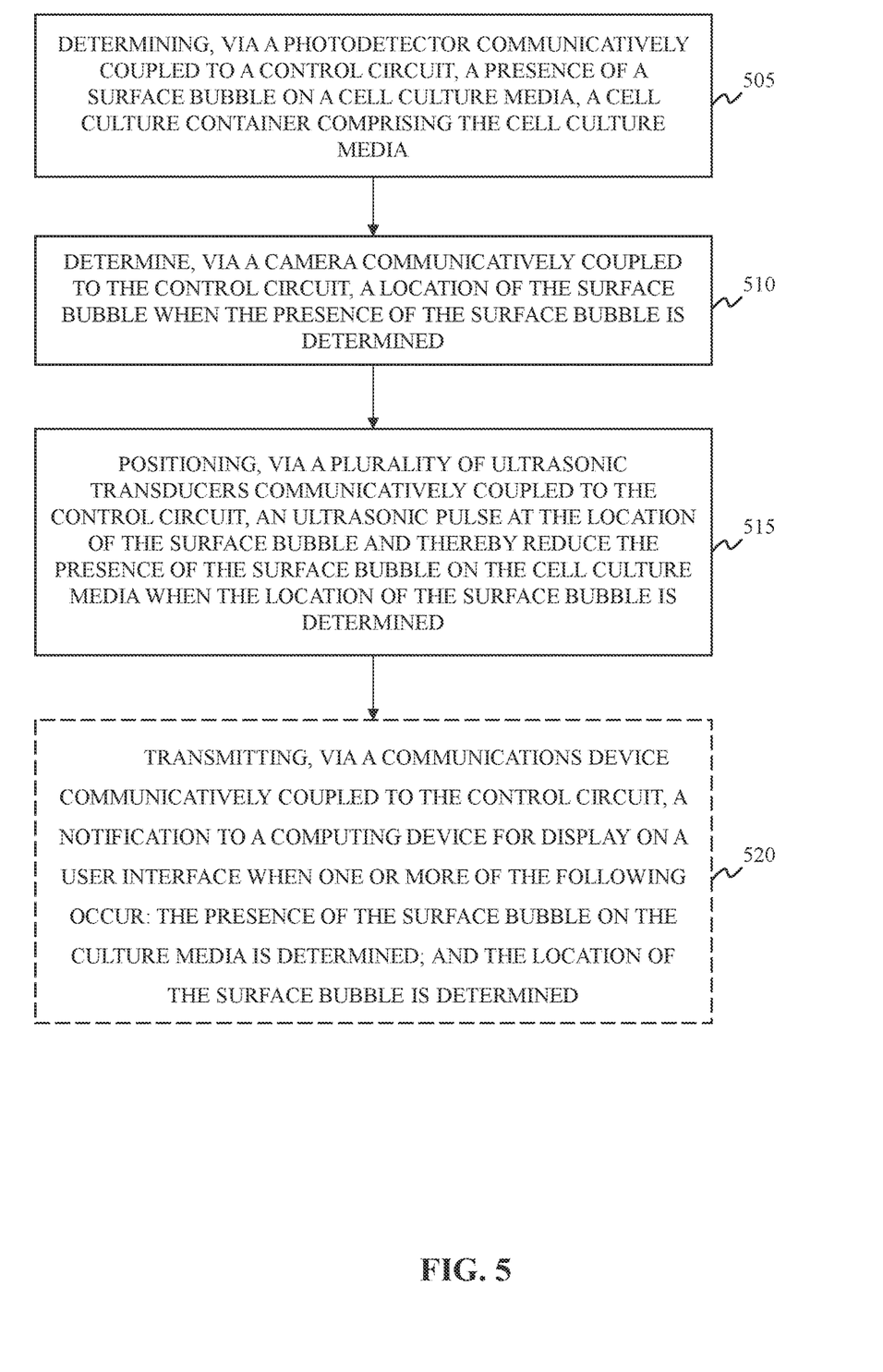
FIG. 5 depicts process steps of a method to reduce surface bubbles from cell culture media, according to some embodiments.
Figure 6:
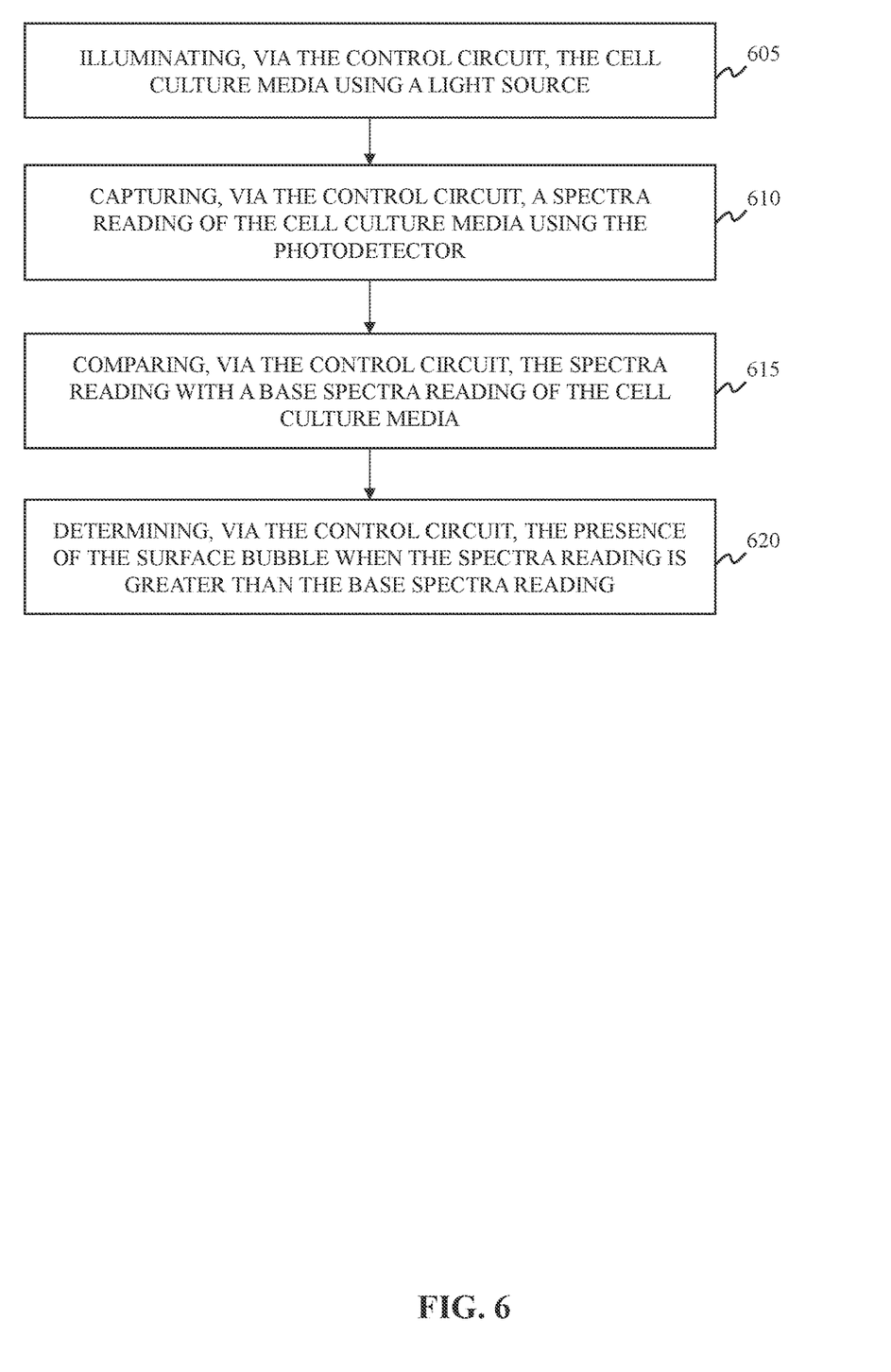
FIG. 6 illustrates process steps of a method to accomplish Step 505 of FIG. 5, according to other embodiments.

FIG. 5 illustrates process steps of a method to reduce surface bubbles from cell culture media, according to yet still other embodiments. At Step 505, determining, via a photodetector 110 communicatively coupled to a control circuit, the presence of a surface bubble 225 on a cell culture media 220 is determined. Here, the cell culture media 220 is included in a cell culture container 215. FIG. 6 illustrates process steps of a method to accomplish Step 505, according to preferred embodiments. At Step 605, illuminating, via the control circuit, the cell culture media 220 is illuminated using a light source 115. At Step 610, capturing, via the control circuit, a spectra reading of the cell culture media 220 is captured using the photodetector 110. At Step 615, comparing, via the control circuit, the spectra reading is compared with a base spectra reading of the cell culture media 220. At Step 620, determining, via the control circuit, the presence of the surface bubble 225 is determined when the spectra reading is greater than the base spectra reading.

Figure 7:
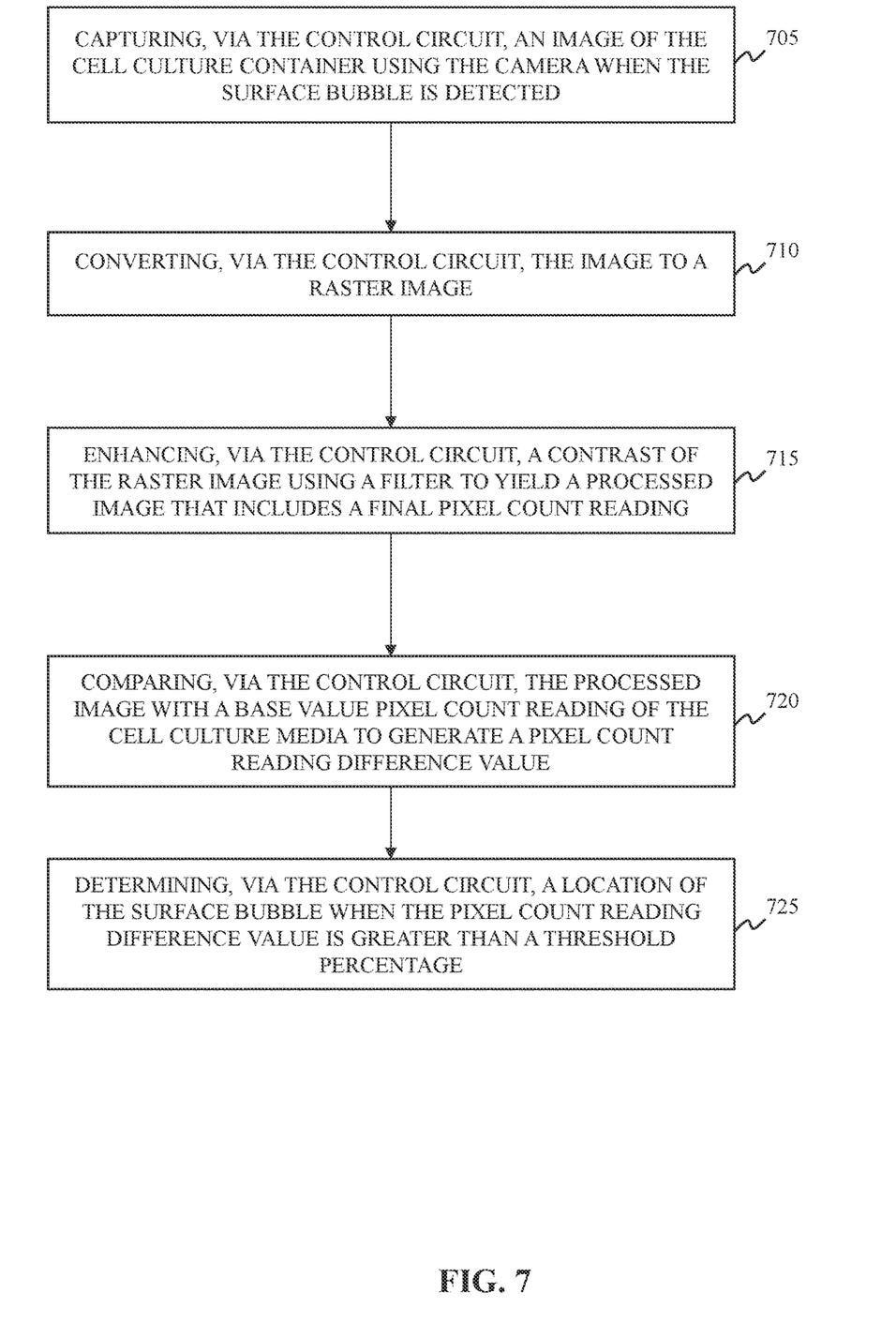
FIG. 7 illustrates process steps of a method to accomplish Step 510 of FIG. 5, according to certain embodiments.

At Step 510, location of the surface bubble 225 is determined when the presence of the surface bubble 225 is determined using a photodetector 110. FIG. 7 illustrates process steps of a method to accomplish Step 510, according to preferred embodiments. At Step 705, capturing, via the control circuit, an image of the cell culture container 215 is captured using a camera 120 when the surface bubble 225 is detected. At Step 710, the image is converted to a raster image. At Step 715, the contrast of the raster image is enhanced using a filter to yield a processed image that includes a final pixel count reading. At Step 720, the processed image is compared with a base value pixel count reading of the cell culture media to generate a pixel count reading difference value. At Step 725, determining, via the control circuit, the location of the surface bubble 225 is determined when the pixel count reading difference value is greater than a threshold percentage.

Figure 8:
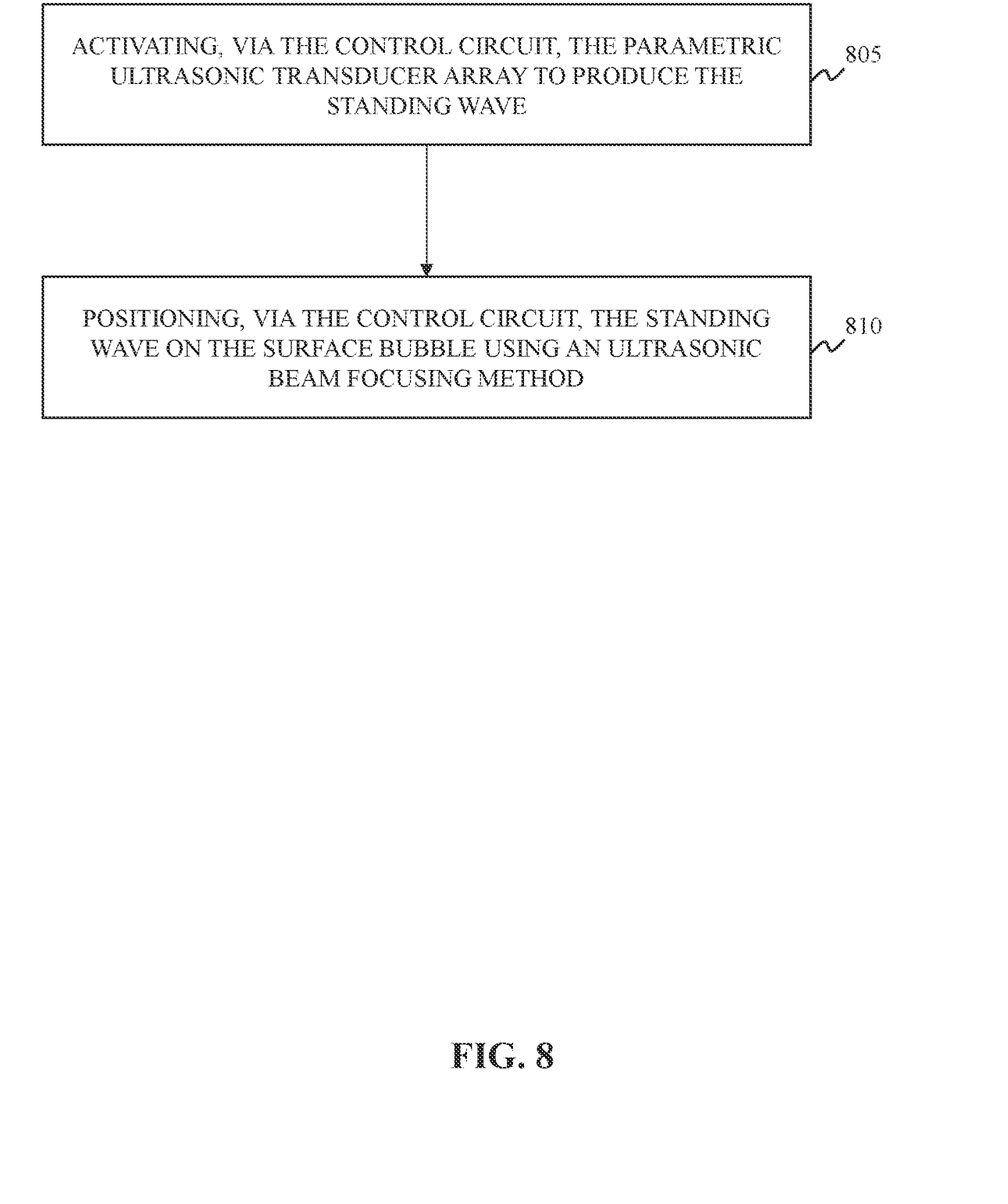
FIG. 8 illustrates process steps of a method to accomplish Step 515 of FIG. 5, according to yet still other embodiments.

At Step 515, an ultrasonic pulse is positioned at the location of the surface bubble using a plurality of ultrasonic transducers 125 and thereby reduce the presence of the surface bubble 225 on the cell culture media 220 when the location of the surface bubble 225 is determined. FIG. 8 illustrates process steps of a method to accomplish Step 515, according to preferred embodiments. At Step 805, the parametric ultrasonic transducer array 205 is activated to produce the standing wave 305. At Step 810, positioning, via the control circuit, the standing wave 305 is positioned on to the surface bubble 225 using an ultrasonic beam focusing method. In preferred embodiments, at Step 520, a communications device 130 is used to transmit a notification to a computing device 150 for display on a user interface 151 when the presence of the surface bubble 225 on the culture media 220 is determined and/or the location of the surface bubble 225 is determined.

Although there are many solutions to achieve Step 505, FIG. 6 illustrates process steps of a method to achieve Step 505, according to preferred embodiments.

Figure 4:
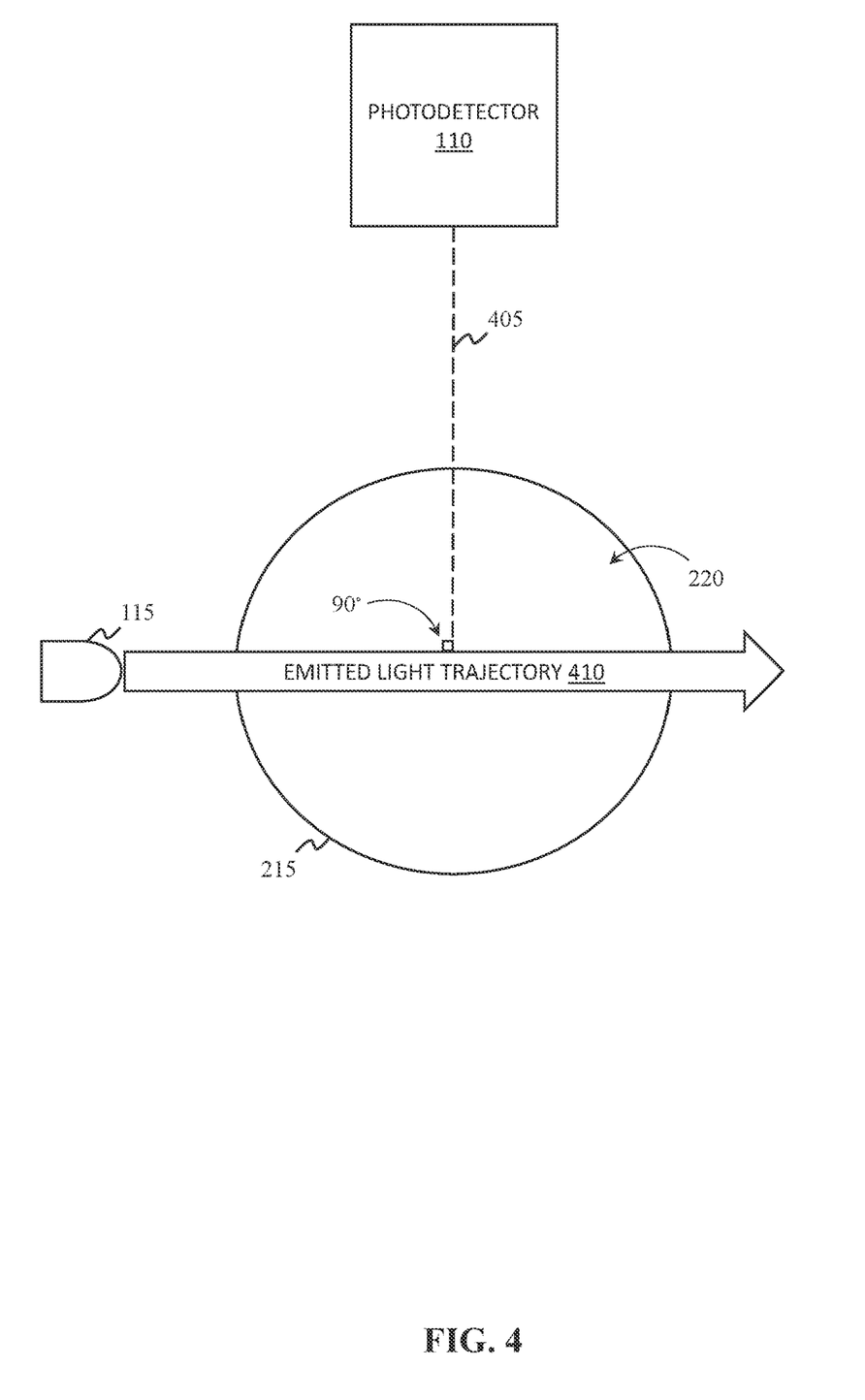
FIG. 4 illustrates a top view of a photodetector positioned proximate to the cell culture container, according to yet still other embodiments.

FIG. 4 illustrates a top view of the cell culture container 215 positioned proximate to the light source 115 and the photodetector 110, according to certain embodiments. The light source 115 is preferably a light source whose wavelength is non-harmful to live cells at short exposure. The photodetector 110 is a device that utilizes typical side scatter light detection. The system 101 utilizes the photodetector 110 to perform spectral identification and identify the change in spectra readings due to the presence of surface air bubble (e.g., the surface bubbles 225) withing the cell culture media 220. The photodetector 110 measures light at ninety-degrees (90°) of the incidence line of the emitted light trajectory 410. In other words, the photodetector 110 preferably has an orientation line 405 that is oriented orthogonal to the incidence line of the emitted light trajectory 410.

The I/O device 145 can also be a temperature sensor, which is an important component for cell culture; with live cell cultures typically placed inside incubators measuring temperatures of 37° C. Fluctuations of temperatures may elicit behavioral changes within a particular cell culture, risk contamination, or if prolonged, kill the cell samples. As a temperature sensor, the I/O device 145 is preferably positioned within the housing 140. For example, the I/O device 145 has a measurement range between −20 to +85° C., with an accuracy of 0.5°, and a field of view of 20°.

Figure 9:
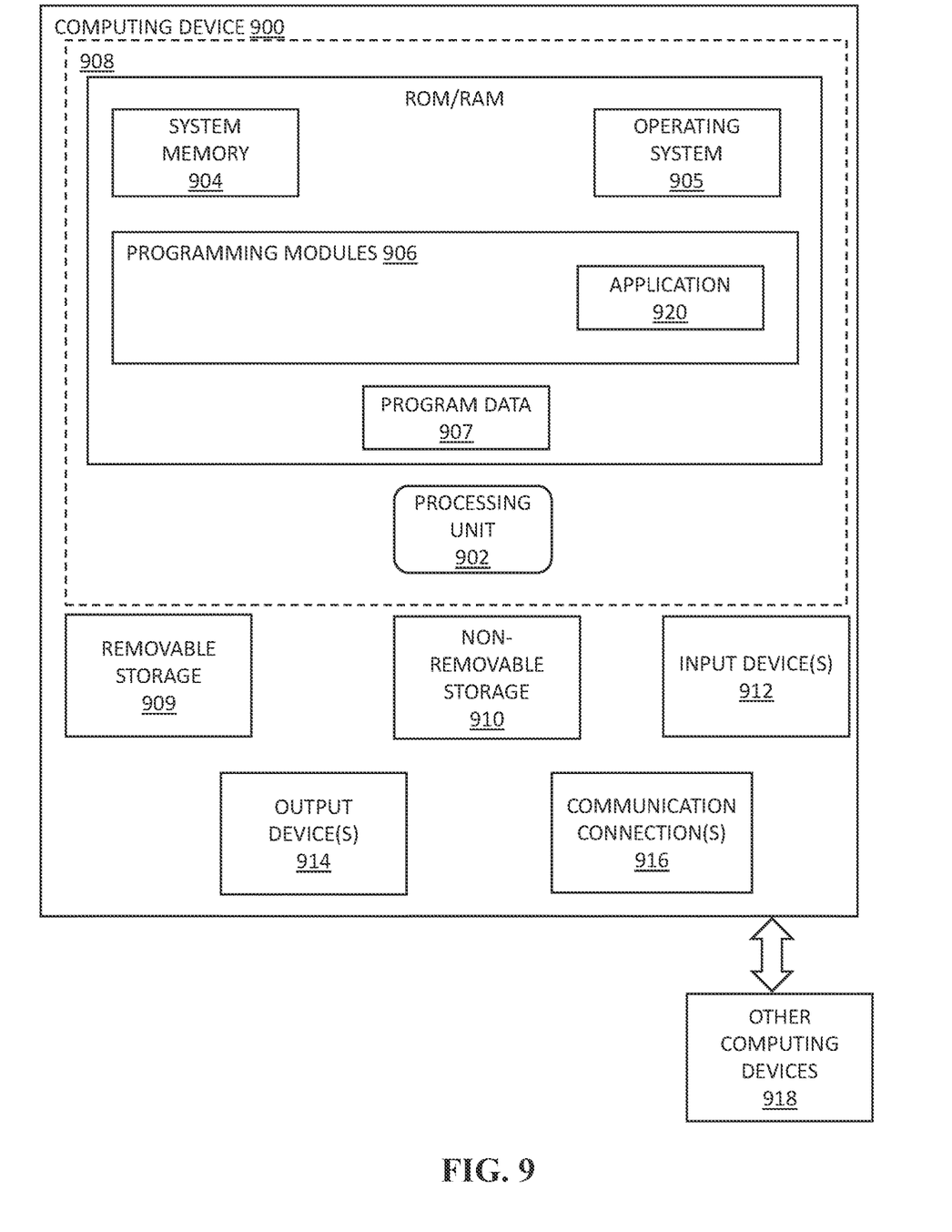
FIG. 9 depicts a block diagram of an exemplary system, according to some embodiments.

With reference to FIG. 9, a system consistent with an embodiment of the disclosure may include a computing device or cloud service, such as computing device 900. Computing device 900 can represent the system 101 and computing device 150. In a basic configuration, computing device 900 may include at least one processing unit 902 (e.g., control circuit 105) and a system memory 904. Depending on the configuration and type of computing device, system memory 904 may comprise, but is not limited to, volatile (e.g., random-access memory (RAM)), non-volatile (e.g., read-only memory (ROM)), flash memory, or any combination. System memory 904 may include operating system 905, one or more programming modules 906, and may include a program data 907. Operating system 905, for example, may be suitable for controlling computing device 900's operation. In one embodiment, programming modules 906 may include machine learning module. Furthermore, embodiments of the disclosure may be practiced in conjunction with a graphics library, other operating systems, or any other application program and is not limited to any particular application or system. This basic configuration is illustrated in FIG. 9 by those components within a dashed line 908.

Computing device 900 may have additional features or functionality. For example, computing device 900 may also include additional data storage devices (removable and/or non-removable) such as, for example, magnetic disks, optical disks, or tape. Such additional storage is illustrated in FIG. 9 by a removable storage 909 and a non-removable storage 910. Computer storage media may include volatile and nonvolatile, removable and non-removable media implemented in any method or technology for storage of information, such as computer-readable instructions, data structures, program modules, or other data. System memory 904, removable storage 909, and non-removable storage 910 are all computer storage media examples (i.e., memory storage). Computer storage media may include, but is not limited to, RAM, ROM, electrically erasable programmable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 900. Any such computer storage media may be part of device 900. Computing device 900 may also have input device(s) 912 such as a keyboard, a mouse, a pen, a sound input device, a touch input device, a location sensor, a camera, a biometric sensor, etc. Output device(s) 914 such as a display, speakers, a printer, etc. may also be included. The aforementioned devices are examples and others may be used.

Computing device 900 may also contain a communication connection 916 that may allow device 900 to communicate with other computing devices 918, such as over a network in a distributed computing environment, for example, an intranet or the Internet. Communication connection 916 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 904, including operating system 905. While executing on processing unit 902 (e.g., control circuit 105), programming modules 906 (e.g., user interface 151) may perform processes including, for example, one or more stages of methods, algorithms, systems, applications, servers, databases as described above.

The aforementioned process is an example, and processing unit 902 (e.g., control circuit 105) may perform other processes. Other programming modules that may be used in accordance with embodiments of the present disclosure may include machine learning application.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the disclosure has been explained in relation to its preferred embodiment, it is to be understood that many other possible modifications and variations can be made without departing from the spirit and scope of the disclosure.

What is claimed is:

1. A system to reduce surface bubbles from cell culture media using ultrasonic pulses, the system comprising:
   a plurality of ultrasonic transducers;
   a photodetector;
   a camera;
   a control circuit;
   a cell culture container comprising a cell culture media;
   wherein the control circuit is communicatively coupled to the plurality of ultrasonic transducers, the temperature sensor, and the camera;
   wherein the control circuit is configured to:
      determine, via the photodetector, a presence of a surface bubble on the cell culture media;
      determine, via the camera, a location of the surface bubble when the presence of the surface bubble is determined;
      position, via the plurality of ultrasonic transducers, an ultrasonic pulse at the location of the surface bubble and thereby reduce the presence of the surface bubble on the cell culture media when the location of the surface bubble is determined.

2. The system of claim 1, wherein to determine the presence of the surface bubble the control circuit is configured to:
   illuminate, via a light source communicatively coupled to the control circuit, the cell culture media;
   capture, via the photodetector, a spectra reading of the cell culture media;
   compare the spectra reading with a base spectra reading of the cell culture media; and
   determine the presence of the surface bubble when the spectra reading is greater than the base spectra reading.

3. The system of claim 2, wherein to determine the location of the surface bubble the control circuit is configured to:
- capture, via the camera, an image of the cell culture container when the surface bubble is detected;
- convert the image to a raster image;
- enhance a contrast of the raster image using a filter to yield a processed image comprising a final pixel count reading;
- compare the processed image with a base value pixel count reading of the cell culture media to generate a pixel count reading difference value;
- determine a location of the surface bubble when the pixel count reading difference value is greater than a threshold percentage.

4. The system of claim 3, wherein
the plurality of ultrasonic transducers is arranged as a parametric ultrasonic transducer array that produces a standing wave when activated.

5. The system of claim 4, wherein
in positioning the ultrasonic pulse, the control circuit is configured to:
- activate the parametric ultrasonic transducer array to produce the standing wave; and
- position the standing wave on the surface bubble using an ultrasonic beam focusing method.

6. The system of claim 5, wherein
the surface bubble comprises a bubble resonant frequency;
the standing wave comprises a beam resonant frequency; and
the presence of surface bubble is reduced when the beam resonant frequency matches the bubble resonant frequency.

7. The system of claim 6, wherein
the plurality of ultrasonic transducers is concavely arranged proximate to the cell culture container.

8. The system of claim 7, wherein
the light source is oriented orthogonal to the photodetector.

9. The system of claim 8, further comprising:
a communications device communicatively coupled to the control circuit;
wherein the control circuit is configured to:
- transmit, via the communications device, a notification when one or more of the following occur:
  - the presence of the surface bubble on the culture media is determined; and
  - the location of the surface bubble is determined.

10. A method to reduce surface bubbles from cell culture media, the method comprising:
- determining, via a photodetector communicatively coupled to a control circuit, a presence of a surface bubble on a cell culture media, a cell culture container comprising the cell culture media;
- determine, via a camera communicatively coupled to the control circuit, a location of the surface bubble when the presence of the surface bubble is determined; and
- positioning, via a plurality of ultrasonic transducers communicatively coupled to the control circuit, an ultrasonic pulse at the location of the surface bubble and thereby reduce the presence of the surface bubble on the cell culture media when the location of the surface bubble is determined.

11. The method of claim 10, wherein determining the presence of the surface bubble comprises:
- illuminating, via the control circuit, the cell culture media using a light source;
- capturing, via the control circuit, a spectra reading of the cell culture media using the photodetector;
- comparing, via the control circuit, the spectra reading with a base spectra reading of the cell culture media; and
- determining, via the control circuit, the presence of the surface bubble when the spectra reading is greater than the base spectra reading.

12. The method of claim 11, wherein determining the location of the surface bubble comprises:
- capturing, via the control circuit, an image of the cell culture container using the camera when the surface bubble is detected;
- converting, via the control circuit, the image to a raster image;
- enhancing, via the control circuit, a contrast of the raster image using a filter to yield a processed image that includes a final pixel count reading;
- comparing, via the control circuit, the processed image with a base value pixel count reading of the cell culture media to generate a pixel count reading difference value;
- determining, via the control circuit, a location of the surface bubble when the pixel count reading difference value is greater than a threshold percentage.

13. The method of claim 12, wherein
the plurality of ultrasonic transducers arranged a parametric ultrasonic transducer array that produces a standing wave when activated.

14. The method of claim 13, wherein positioning the ultrasonic pulse comprises:
- activating, via the control circuit, the parametric ultrasonic transducer array to produce the standing wave; and
- positioning, via the control circuit, the standing wave on the surface bubble using an ultrasonic beam focusing method.

15. The method of claim 14, wherein
the surface bubble comprises a bubble resonant frequency;
the single standing wave comprises a beam resonant frequency;
the presence of the surface bubble is reduced when the bubble resonant frequency matches the beam resonant frequency.

16. The method of claim 15, wherein
the plurality of ultrasonic transducers is concavely arranged and positioned proximate to the cell culture container.

17. The method of claim 16, wherein
the light source is oriented orthogonal to the photodetector.

18. The method of claim 17, further comprising:
transmitting, via a communications device communicatively coupled to the control circuit, a notification to a computing device for display on a user interface when one or more of the following occur:
the presence of the surface bubble on the culture media is determined; and
the location of the surface bubble is determined.

* * * * *